(12) United States Patent
Okano et al.

(10) Patent No.: US 6,495,645 B1
(45) Date of Patent: Dec. 17, 2002

(54) ACRYLAMIDE DERIVATIVES AND POLYMERS CONTAINING SAID DERIVATIVES

(75) Inventors: Teruo Okano, Chiba (JP); Takao Aoyagi, Chiba (JP)

(73) Assignee: Terou Okano, Ichikawa (JP)

( * ) Notice: Subject to any disclaimer, the term of this patent is extended or adjusted under 35 U.S.C. 154(b) by 0 days.

(21) Appl. No.: 09/889,953

(22) PCT Filed: Jan. 24, 2000

(86) PCT No.: PCT/JP00/00314
§ 371 (c)(1),
(2), (4) Date: Aug. 30, 2001

(87) PCT Pub. No.: WO00/43355
PCT Pub. Date: Jul. 27, 2000

(30) Foreign Application Priority Data

Jan. 25, 1999 (JP) .......................................... 11-015827

(51) Int. Cl.[7] ............................................. C08F 122/38
(52) U.S. Cl. .............................. 526/307.7; 526/303.1; 526/314; 526/305; 526/307; 526/307.1; 526/307.2; 526/307.5
(58) Field of Search .............................. 526/303.1, 304, 526/305, 307, 307.1, 307.2, 307.5, 307.7

(56) References Cited

U.S. PATENT DOCUMENTS

| | | | |
|---|---|---|---|
| 5,155,191 A | * 10/1992 | Itoh et al. | 526/226 |
| 5,244,763 A | * 9/1993 | Nielsen et al. | 430/72 |
| 5,698,627 A | * 12/1997 | Oguni et al. | 524/724 |
| 5,700,892 A | * 12/1997 | Takiguchi et al. | 526/306 |
| 6,069,216 A | * 5/2000 | Iwasaki et al. | 526/258 |
| 6,268,449 B1 | * 7/2001 | Chang et al. | 526/212 |

FOREIGN PATENT DOCUMENTS

| WO | WO9112230 | 8/1991 |
|---|---|---|

OTHER PUBLICATIONS

Okano et al., J. Biomedical Materials Research, vol. 27 (1993) pp. 1243–1251.

Okano et al., Biomaterials, vol. 16, No. 4 (1995) pp. 297–303.

Kanazawa et al., Analytical Chemistry, vol. 68, No. 1 (1996) pp. 100–105.

Kanazawa et al., Analytical Chemistry, vol. 69, No. 5 (1997) pp. 823–830.

Koyama E. et al., "Syntheses and Radical Polymerizations of Methacrylamides derived from Optically active amino Alcohols", Macromolecular Chemistry and Physics, vol. 198, No. 11, Nov. 1, 1997, pp. 3699–3707.

Beger J. et al., "Halogenierung Von Olefinen In Gegenwart Organischer Cyanverbindungen", Journal Fuer Praktische Chemie, vol. 311, Jan. 1, 1969, pp. 15–35.

Meyers, A.I. et al., "The synthesis of chiral. alpha.,. beta.–unsaturated and aryl oxazolines from ketones and arols via their triflates and palladium–catalyzed carbon monoxide and amino alcohol coupling", Tetrahedron Lett, 1992, p. 1182; figure 5 and p. 1183.

* cited by examiner

Primary Examiner—Helen L. Pezzuto
(74) Attorney, Agent, or Firm—Birch, Stewart, Kolasch & Birch, LLP

(57) ABSTRACT

An acrylamide derivative of the following general formula (I) is used to prepare a polymer or copolymer:

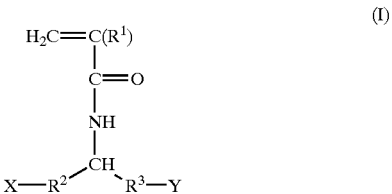

wherein $R^1$ represents a hydrogen atom, a straight-chain or branched alkyl group containing 1 to 4 carbon atoms or a C3–6 cycloalkyl group, $R^2$ and $R^3$ each independently represent an alkylene group containing 1 to 6 carbon atoms or $R^2$ and $R^3$ may be combined to form a ring, X represents a hydrogen atom, an amino group, a hydroxyl group, a halogen atom, a carboxyl group or a —COOR$^4$ group wherein $R^4$ represents a C1–6 straight-chain or branched alkyl, C3–6 cycloalkyl, phenyl, substituted phenyl, benzyl or substituted benzyl group, and Y represents an amino group, a halogen atom, a carboxyl group or a —COOR$^4$ group wherein $R^4$ represents a C1–6 straight-chain or branched alkyl, C3–6 cycloalkyl, phenyl, substituted phenyl, benzyl or substituted benzyl group. The thus obtained polymer or copolymer is a polymer or hydrogel incorporating many functional groups while maintaining the sensitive temperature response.

10 Claims, 3 Drawing Sheets

ACRYLAMIDE DERIVATIVES AND POLYMERS CONTAINING SAID DERIVATIVES

This application is the national phase under 35 U.S.C. §371 of PCT International Application No. PCT/JP00/00314 which has an International filing date of Jan. 24, 2000, which designated the United States of America and was published in English.

TECHNICAL FIELD

The present invention relates to acrylamide derivatives having functional groups on side chains, homopolymers and copolymers of said derivatives, as well as crosslinked products of said polymers. Acrylamide derivatives of the present invention can readily be radical-polymerized to conveniently prepare homopolymers and can also be copolymerized with other monomers. Copolymers synthesized from acrylamide derivatives of the present invention can be temperature-responsive polymers, which are soluble below but insolubilized above a specific temperature in aqueous solutions. Thus, they can be immobilized on the surface of a solid to show hydrophilicity and hydrophobicity below and above the specific temperature, respectively. Copolymers of the present invention can be used not only to switch between hydrophilicity and hydrophobicity in a narrow temperature range but also to switch from an electrically charged state to a non-charged state simply by temperature change. Moreover, their various functional groups can be used to introduce various molecules via covalent or hydrogen bonds.

BACKGROUND ART

N-alkyl-substituted acrylamide polymers are one of temperature-responsive polymers, among which poly(N-isopropyl acrylamide) (hereinafter abbreviated as PIPAAm) is water-soluble below but rapidly insolubilized to form a precipitate above the phase transition temperature of 32° C. Sequences of PIPAAm have been introduced into the surfaces of solids to switch between hydrophilicity and hydrophobicity simply by temperature change for harvesting cells after culture or development into chromatography. Such techniques are described in the following documents, for example:

T. Okano, N. Yamada, H. Sakai, Y. Sakurai, Journal of Biomedical Materials Research, vol. 27, pp. 1243–1251 (1993);

T. Okano, N. Yamada, M. Okuhara, H. Sakai, Y. Sakurai, Biomaterials, vol. 16, pp. 297–303 (1995);

H. Kanazawa, K. Yamamoto, Y. Matsushima, N. Takai, A. Kikuchi, Y. Sakurai, T. Okano, Analytical Chemistry, vol. 68, pp. 100–105 (1996);

H. Kanazawa, Y. Kashiwase, K. Yamamoto, Y. Matsushima, A. Kikuchi, Y. Sakurai, T. Okano, Analytical Chemistry, vol. 69, pp. 823–830 (1997).

These temperature-responsive polymers are commonly copolymerized with comonomers having a functional group such as acrylic acid to introduce the functional group into said polymers. However, straight-chain polymers or hydrogels (i.e. crosslinked products) incorporating an increased rate of acrylic acid inevitably showed a significant rise in phase transition temperature and insensitive transition behaviors. Namely, no method has existed for introducing many functional groups into temperature-responsive polymers or hydrogels while maintaining the sensitive temperature response.

DISCLOSURE OF INVENTION

An object of the present invention is to provide a monomer for preparing a polymer or hydrogel (i.e. crosslinked product) incorporating many functional groups while maintaining the sensitive temperature response, and said polymer or hydrogel (i.e. crosslinked product).

We carefully studied to solve the above problems. As a result, we found that the temperature response of homopolymers can be maintained by copolymerizing them with a monomer having a closely similar structure to that of the homopolymers, and thus attained the present invention.

Accordingly, the present invention provides acrylamide derivatives of the following general formula (I):

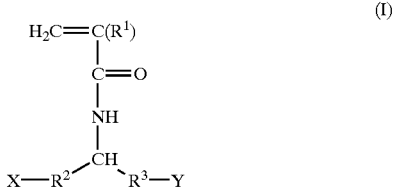

(I)

wherein $R^1$ represents a hydrogen atom, a straight-chain or branched alkyl group containing 1 to 6 carbon atoms or a C3–6 cycloalkyl group, $R^2$ and $R^3$ each independently represent an alkylene group containing 1 to 6 carbon atoms or $R^2$ and $R^3$ may be combined to form a ring, X represents a hydrogen atom, an amino group, a hydroxyl group, a halogen atom, a carboxyl group or a —COOR$^4$ group wherein $R^4$ represents a C1–6 straight-chain or branched alkyl, C3–6 cycloalkyl, phenyl, substituted phenyl, benzyl or substituted benzyl group, and Y represents an amino group, a hydroxyl group, a halogen atom, a carboxyl group or a —COOR$^4$ group wherein $R^4$ represents a C1–6 straight-chain or branched alkyl, C3–6 cycloalkyl, phenyl, substituted phenyl, benzyl or substituted benzyl group.

The present invention also provides polymers consisting of identical or different repeating units of the following general formula (II):

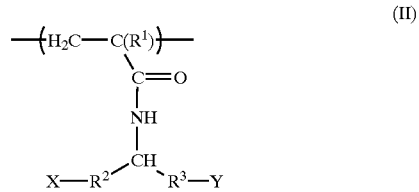

(II)

wherein $R^1$ represents a hydrogen atom, a straight-chain or branched alkyl group containing 1 to 6 carbon atoms or a C3–6 cycloalkyl group, $R^2$ and $R^3$ each independently represent a alkylene group containing 1 to 6 carbon atoms or $R^2$ and $R^3$ may be combined to form a ring, X represents a hydrogen atom, an amino group, a hydroxyl group, a halogen atom, a carboxyl group or a —COOR$^4$ group wherein $R^4$ represents a C1–6 straight-chain or branched alkyl, C3–6 cycloalkyl, phenyl, substituted phenyl, benzyl or substituted benzyl group, and Y represents an amino group, a hydroxyl group, a halogen atom, a carboxyl group or a —COOR$^4$ group wherein $R^4$ represents a C1–6 straight-chain or branched alkyl, C3–6 cycloalkyl, phenyl, substituted phenyl, benzyl or substituted benzyl group.

The present invention also provides copolymers consisting of different or identical repeating units of the above general formula (II) and different or identical repeating units of general formula (III):

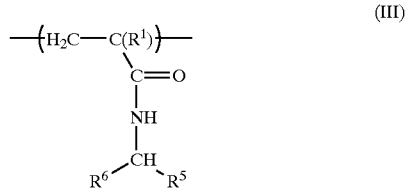

(III)

wherein $R^1$ represents a hydrogen atom, a straight-chain or branched alkyl group containing 1 to 6 carbon atoms or a C3–6 cycloalkyl group, $R^5$ represents a straight-chain or branched alkyl group containing 1 to 6 carbon atoms or a C3–6 cycloalkyl group, and $R^6$ represents a straight-chain or branched alkyl group containing 1 to 6 carbon atoms or a C3–6 cycloalkyl group, or $R^5$ and $R^6$ may be combined to form a 3-, 4-, 5 or 6-membered ring in which the —CH— group to which they are attached is one member.

Additionally, the present invention provides crosslinked products containing said polymers and crosslinked products containing said copolymers.

BEST MODE FOR CARRYING OUT THE INVENTION

Figure 1:
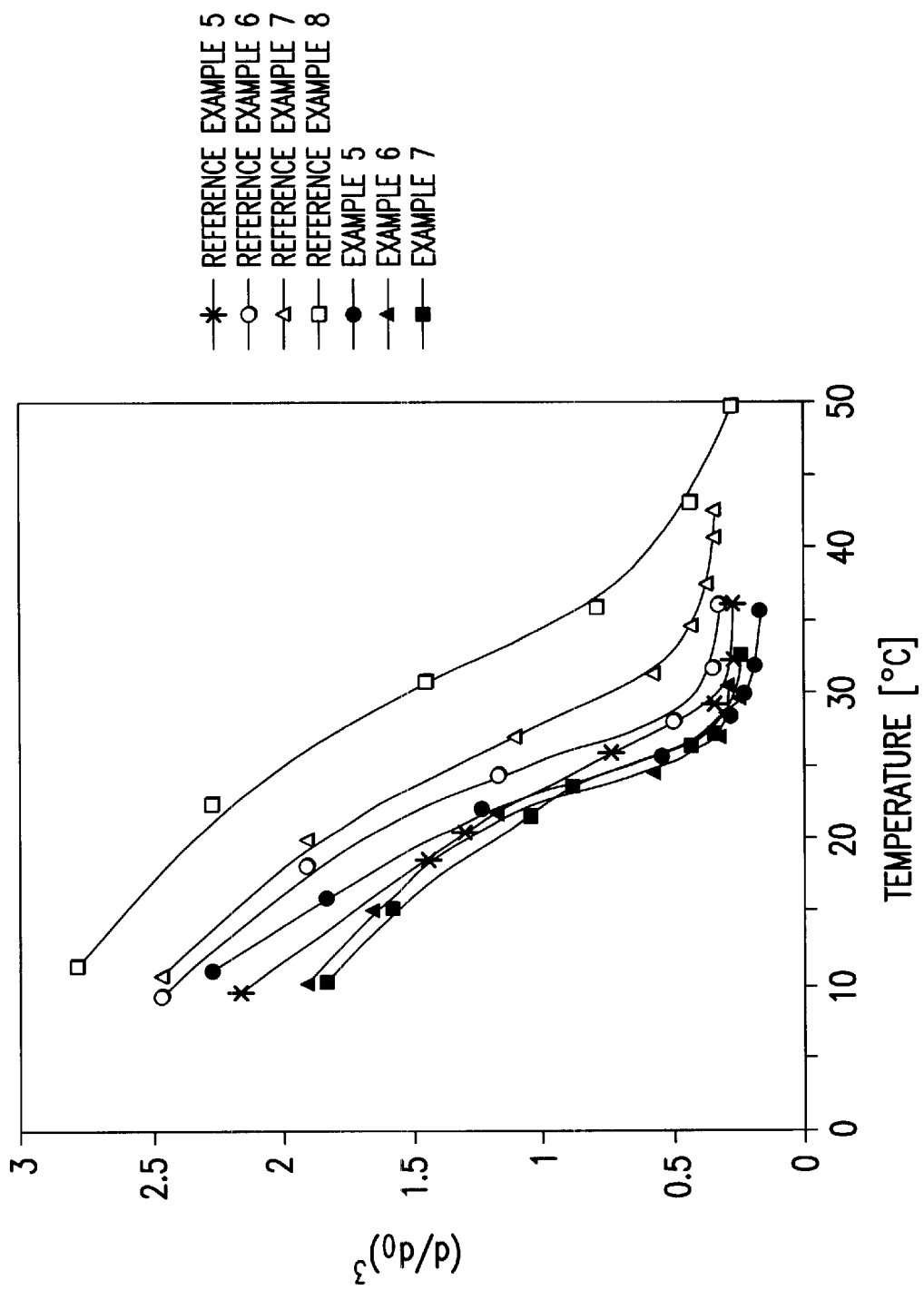
FIG. 1 is a graph showing the equilibrium swell of each crosslinked product in a phosphate buffer at pH 6.4.

In the present invention, the straight-chain or branched alkyl group containing 1 to 6 carbon atoms includes methyl, ethyl, n-propyl, i-propyl, n-butyl, i-butyl, s-butyl, t-butyl, n-pentyl and n-hexyl groups.

In the present invention, the alkylene group containing 1 to 6 carbon atoms includes monomethylene, dimethylene, trimethylene, tetramethylene, pentamethylene and hexamethylene groups. A preferred alkylene group is a monomethylene group.

In the present invention, the halogen atom means any of fluorine, chlorine, bromine and iodine atoms. An especially preferred halogen atom is a chlorine atom.

In the present invention, substituents on the substituted phenyl group are not specifically limited, but include nitro and methylmercapto groups, for example. An especially preferred substituent on the substituted phenyl group is a nitro group.

In the present invention, the substituted benzyl group is not specifically limited, but includes triphenylmethyl and diphenylmethyl groups, for example.

When $R^2$ and $R^3$ are combined to form a ring in general formulae (I) and (II), the ring is preferably cyclopropane, cyclobutane, cyclopentane, cyclohexane, cyclooctane, etc.

In the present invention, the polymerization degree of polymers consisting of repeating units of general formula (II) is not specifically limited so far as the number of repeating units is 2 or more, preferably 50 to 500.

In the present invention, copolymers consisting of repeating units of general formula (II) and repeating units of general formula (III) are not specifically limited so far as the number of each repeating unit is 2 or more, preferably 50 to 500. The ratio of the former to latter repeating units is not specifically limited, either, but the ratio of the number of repeating units of general formula (II) to the number of repeating units of general formula (III) is preferably in the range of 1 to 50:99 to 50.

Processes for preparing an acrylamide derivative as well as a polymer, copolymer and crosslinked product prepared from said derivative are now described.

An acrylamide derivative of the present invention can readily be obtained by, for example, reacting a compound of general formula (IV):

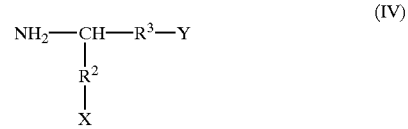

(IV)

wherein $R^2$ represents a straight-chain or branched alkyl group containing 1 to 6 carbon atoms, $R^3$ represents an alkylene group containing 1 to 6 carbon atoms, X represents a hydroxyl group, a halogen atom, a carboxyl group, an ester group represented by —COOR$^4$ wherein $R^4$ represents a C1–6 straight-chain or branched alkyl, phenyl, substituted phenyl, benzyl or substituted benzyl group, or a substituted amino group represented by —NH—R$^7$ wherein $R^7$ represents a C1–6 straight-chain or branched alkyl, a C3–6 cycloalkyl, alkyloxycarbonyl, phenyl, substituted phenyl, benzyl, substituted benzyl, benzyloxycarbonyl or substituted benzyloxycarbonyl group, or $R^2$ and $R^3$ may be combined to form a ring, with a compound of general formula (V):

(V)

wherein $R^1$ represents a hydrogen atom or a straight-chain or branched alkyl group containing 1 to 6 carbon atoms.

The compound of general formula (V) includes acrylic acid, methacrylic acid, α-ethylacrylic acid, α-n-butylacrylic acid and α-n-hexylacrylic acid and some of them are commercially available. This reaction more efficiently proceeds in the presence of a condensation agent such as dicyclohexyl carbodiimide, diisopropyl carbodiimide, N-ethyl-N'-3-dimethylaminopropyl carbodiimide, benzotriazole-1-yl-tris (dimethylamino)phosphonium hexafluorophosphide, diphenylphosphoryl azide, which may be used alone or in combination with N-hydroxysuccinimide, 1-hydroxybenzotriazole, etc. The reaction is desirably carried out in any solvent that dissolves the compounds but does not participate in the reaction, including, but not limited to, water, chloroform, dichloromethane, dichloroethane, benzene, toluene, xylene, acetone, methyl ethyl ketone, tetrahydrofuran, dioxane, ethyl acetate, acetonitrile, dimethyl sulfoxide, N,N-dimethylformamide, N,N-dimethylacetamide, etc. Normally, the reaction smoothly proceeds in a temperature range from 0° C. to 100° C.

If these condensation agents are not used, the reaction readily proceeds by using the compound of general formula (V) converted into an acid halide. The acid halide includes acryloyl chloride, methacryloyl chloride, acryloyl bromide, methacryloyl bromide, and some of them are commercially available. Other acid halides can also be obtained by a known method using thionyl chloride, phosphorus trichloride, phosphorus pentaoxide or the like. The reaction readily proceeds in an organic solvent under an inert gas atmosphere. Any solvent that does not participate in the reaction may be used, including, but not limited to, chloroform, dichloromethane, dichloroethane, benzene, toluene, xylene, acetone, methyl ethyl ketone, tetrahydrofuran, dioxane, ethyl acetate, acetonitrile, dimethyl sulfoxide, N,N-dimethylformamide, N,N-dimethylacetamide, etc.

This reaction preferably takes place in the presence of a basic material such as lithium hydroxide, potassium hydroxide, sodium hydroxide, aluminium hydroxide, potassium carbonate, sodium carbonate, potassium acetate, sodium acetate, sodium phosphate, sodium hydride, calcium hydride, pyridine, triethylamine, N,N-dimethylaniline, etc.

Suitable compounds of general formula (IV) include 1-(hydroxymethyl) ethylamine, 1-(hydroxymethyl) propylamine, β-aminobutyric acid, β-aminobutyric acid methyl ester, β-aminobutyric acid p-nitrophenyl ester, β-aminobutyric acid benzyl ester, 2-aminopropyl chloride, 2-aminopropyl bromide, γ-aminovaleric acid, γ-aminovaleric acid methyl ester, γ-aminovaleric acid p-nitrophenyl ester, γ-aminovaleric acid benzyl ester, β-aminovaleric acid, β-aminovaleric acid benzyl ester, 1-methylamino-2-aminopropane, 1-(t-butoxycarbonyl) amino-2-aminopropane, 1-benzylamino-2-aminopropane, 1-(benzyloxycarbonyl) amino-2-aminopropane. Some of them are commercially available.

Acrylamide derivatives of general formula (I) of the present invention can be homopolymerized to prepare a polymer consisting of repeating units of general formula (II) by a conventional polymerization method, more conveniently by radical polymerization. The radical polymerization can be performed by a known method such as bulk polymerization, solution polymerization and emulsion polymerization, and efficiently initiated by addition of a radical initiator. Preferably suitable radical initiators for the reaction include inorganic peroxides such as potassium persulfate, ammonium persulfate, which may be used in combination with amine compounds called as polymerization promoters such as N,N,N',N'-tetramethylethylenediamine, N,N-dimethylparatoluidine to allow rapid polymerization at lower temperatures. Organic peroxides such as dilauroyl peroxide, benzoyl peroxide, di-t-butyl peroxide, t-butyl hydroperoxide, cumene hydroperoxide or azo compounds such as α,α-azobisisobutyronitrile or azobiscyclohexane carbonitrile are also suitable.

Suitable solvents for the radical polymerization reaction here include, but not limited to, water, methanol, ethanol, normal propanol, isopropanol, 1-butanol, isobutanol, hexanol, benzene, toluene, xylene, chlorobenzene, dichloromethane, chloroform, carbon tetrachloride, acetone, methyl ethyl ketone, tetrahydrofuran, dioxane, acetonitrile, dimethyl sulfoxide, N,N-dimethylformamide, N,N-dimethylacetamide, etc. Normally, the reaction smoothly proceeds in a temperature range from 0° C. to 100° C.

Copolymers consisting of repeating units of general formula (III) and repeating units of general formula (III) can readily be synthesized by copolymerizing a compound of general formula (I) with, for example, isopropyl acrylamide, isobutyl acrylamide, 3-pentyl acrylamide, cyclopentyl acrylamide, 3-hexyl acrylamide or the like. They can be prepared by a conventional polymerization method, more conveniently by radical polymerization. The radical polymerization can be performed by a known method such as bulk polymerization, solution polymerization or emulsion polymerization and efficiently initiated by addition of a radical initiator. Preferably suitable radical initiators for the reaction include inorganic peroxides such as potassium persulfate or ammonium persulfate, which may be used in combination with amine compounds called as polymerization promoters such as N,N,N',N'-tetramethylethylenediamine, N,N-dimethylparatoluidine to allow rapid polymerization at lower temperatures. Other examples include, but not limited to, organic peroxides such as dilauroyl peroxide, benzoyl peroxide, di-t-butyl peroxide, t-butyl hydroperoxide, cumene hydroperoxide or azo compounds such as α,α-azobisisobutyronitrile or azobiscyclohexane carbonitrile.

Suitable solvents for the radical polymerization reaction here include, but not limited to, water, methanol, ethanol, normal propanol, isopropanol, 1-butanol, isobutanol, hexanol, benzene, toluene, xylene, chlorobenzene, dichloromethane, chloroform, carbon tetrachloride, acetone, methyl ethyl ketone, tetrahydrofuran, dioxane, acetonitrile, dimethyl sulfoxide, N,N-dimethylformamide, N,N-dimethylacetamide, etc. Normally, the reaction smoothly proceeds in a temperature range from 0° C. to 100° C.

Crosslinked products containing repeating units of general formula (II) and crosslinked products containing a copolymer consisting of repeating units of general formulae (II) and (III) can readily be obtained by polymerization reaction in the presence of a polyfunctional compound commonly called as a crosslinking agent. The crosslinking agent includes methylene bisacrylamide, ethylene glycol dimethacrylate, glycerin triacrylate, glycerin trimethacrylate, trimethylolpropane triacrylate, pentaerythritol tetraacrylate, etc. and some of them are commercially available. They can be prepared by a conventional polymerization method, more conveniently by radical polymerization. The radical polymerization can be performed by a known method such as bulk polymerization, solution polymerization and emulsion polymerization, and efficiently initiated by addition of a radical initiator. Preferably suitable radical initiators for the reaction include inorganic peroxides such as potassium persulfate, ammonium persulfate, which may be used in combination with amine compounds called as polymerization promoters such as N,N,N',N'-tetramethylethylenediamine, N,N-dimethylparatoluidine to allow rapid polymerization at lower temperatures. Other examples include, but not limited to, organic peroxides such as dilauroyl peroxide, benzoyl peroxide, di-t-butyl peroxide, t-butyl hydroperoxide, cumene hydroperoxide or azo compounds such as α,α-azobisisobutyronitrile or azobiscyclohexane carbonitrile.

Suitable solvents for the radical polymerization reaction here include, but not limited to, water, methanol, ethanol, normal propanol, isopropanol, 1-butanol, isobutanol, n-hexanol, benzene, toluene, xylene, chlorobenzene, dichloromethane, chloroform, carbon tetrachloride, acetone, methyl ethyl ketone, tetrahydrofuran, dioxane, acetonitrile, dimethyl sulfoxide, N,N-dimethylformamide, N,N-dimethylacetamide. Normally, the reaction smoothly proceeds in a temperature range from 0° C. to 100° C.

The temperature response of polymers obtained by the present invention can be evaluated by dissolving them in water or a buffer solution and then determining the temperature range required for the solution to complete turbidity change when the temperature of the solution was changed at a constant rate. As to crosslinked products, they can be evaluated by the change in degree of equilibrium swell with temperature change.

EXAMPLES

The present invention will now be explained in more detail by examples, comparative examples and reference examples which are naturally not intended to limit the present invention.

References Examples 1 to 4

In 35 ml of tetrahydrofuran were dissolved N-isopropyl acrylamide (abbreviated as "IPAAm") and acrylic amide (abbreviated as "AAc") in respective amounts as described in Table 1 and 11.5 mg of azobisisobutyronitrile (abbreviated as "AIBN") as the polymerization initiator, deaerated, then sealed and stirred at 65° C. for 2.5 hours. After the reaction, the precipitation of the reaction product into diethyl ether was twice repeated to effect purification.

TABLE 1

Synthesis of N-Isopropyl Acrylamide/Acrylic Acid copolymers

| Reference Example | Molar Ratio of IPAAm to AAc | Amount of IPAAm (g) | Amount of AAc (g) | Yield (g) |
|---|---|---|---|---|
| 1 | 100:0 | 5.650 | 0 | 4.295 |
| 2 | 97:3 | 5.488 | 0.108 | 2.649 |
| 3 | 95:5 | 5.375 | 0.180 | 4.111 |
| 4 | 90:10 | 5.092 | 0.360 | 2.083 |

Reference Examples 5 to 8

In a test tube N-isopropyl acrylamide (abbreviated as "IPAAm") and acrylic acid (abbreviated as "AAc") in respective amounts as described in Table 2, 26.6 mg of methylenebisacrylamide as the crosslinking agent and 48 μl of N,N,N',N'-tetramethylenediamine as the polymerization promoter were dissolved in 10 ml of water. After the resulting solution was bubbled with a nitrogen gas, 200 μl of a 40 mg/ml ammonium persulfate aqueous solution were immediately added thereto and then, the solution was drawn up in a capillary tube. The capillary tube was maintained at 0° C. for 24 hours and then, a crosslinked product thus prepared was taken out of the capillary and dipped in cold water for one day to effect purification.

TABLE 2

Preparation of N-Isopropyl Acrylamide/Acrylic Acid Copolymerization Crosslinked Products

| Reference Example | Molar Ratio of IPAAm to AAc | Amount of IPAAm (g) | Amount of AAc (ml) |
|---|---|---|---|
| 5 | 100:0 | 1.569 | 0 |
| 6 | 99:1 | 1.553 | 0.009 |
| 7 | 97:3 | 1.524 | 0.029 |
| 8 | 95:5 | 1.509 | 0.048 |

Example 1

Synthetic Scheme of 2-(Benzyloxycarbonyl) isopropyl Acrylamide

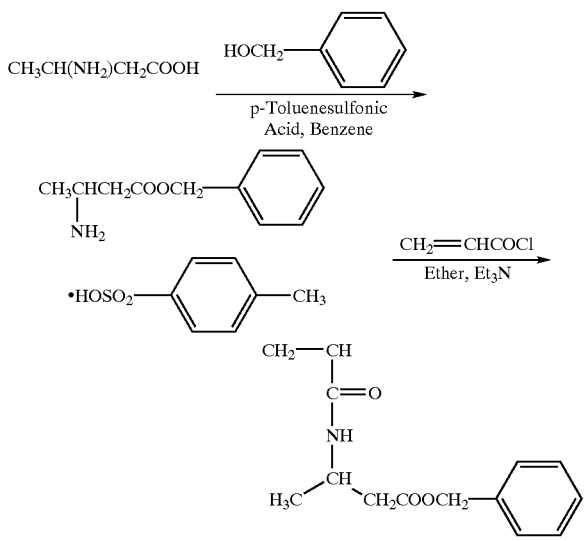

According to the above synthetic scheme, first, 18.1 g of aminobutyric acid, 87.5 ml of benzyl alcohol and 40.0 g of p-toluenesulfonic acid were dissolved in 175 ml of benzene and refluxed. The water formed was removed as the azeotrope with benzene. To the reaction solution were added 280 ml of diethyl ether and 280 ml of hexane to form a precipitate. This precipitate was separated by filtration and recystallized in an ether/ethanol mixed solution to effect purification. As a result, 53.8 mg of β-aminobutyric acid benzyl ester·p-toluenesulfonate were obtained as a white crystal. From the results of $^1$H-NMR spectrometry the synthesis of β-aminobutyric acid benzyl ester·p-toluenesulfonate was confirmed. The results of the $^1$H-NMR spectrometry are set forth below. The underlined portion shows the position of the corresponding proton in the compound. Further, in the NMR data, "Φ-" shows a phenyl group.

$^1$H-NMR δ (DMSO-d$_6$, ppm) 1.20 (d, 3H, C$\underline{H}_3$CHCH$_2$), 2.29 (s, 3H, Φ-C$\underline{H}_3$), 26.8 (m, 2H, CH$_3$CHC$\underline{H}_2$), 3.54 (m, 1H, CH$_3$C$\underline{H}$CH$_2$), 5.14 (s, 2H, COOC$\underline{H}_2$-Φ), 7.11 and 7.48 (m, 4H, hydrogens on the benzene ring of the p-toluenesulfonate), 7.39 (m, 5H, hydrogens on the benzene ring of the benzyl ester), 7.81 [m, 2H, CH$_3$CH(NH$_2$)C$\underline{H}_2$]

Next, 50 g of β-aminobutyric acid benzyl ester·p-toluenesulfonate were dispersed in 300 ml of ether containing 54.3 ml of triethylamine. To this dispersion were slowly added 12.7 ml of acryloyl chloride at 0° C. and stirred for 2 hours. The ether layer was recovered, condensed and purified by silica gel chromatography to obtain 19.59 g of the desired 2-(benzyloxycarbonyl)isopropyl acrylamide as a white crystal. The synthesis was confirmed by $^1$H-NMR spectrometry and elementary analysis. The results of the $^1$H-NMR spectrometry and the elementary analysis are set forth below. The underlined portion shows the position of the corresponding proton in the compound.

$^1$H-NMR δ (DMSO-d$_6$, ppm) 1.11 (d, 3H, C$\underline{H}_3$CHCH$_2$), 2.53 (m, 2H, CH$_3$CHC$\underline{H}_2$), 4.20 (m, 1H, CH$_3$C$\underline{H}$CH$_2$), 5.06 (s, 2H, COOC$\underline{H}_2$-Φ), 5.55, 6.07 and 6.18 (m, 3H, C$\underline{H}$=C$\underline{H}_2$), 7.35 (m, 5H, hydrogens on the benzene ring), 8.10 (d, 1H, CON$\underline{H}$); Elementary Analysis: C$_{14}$H$_{17}$NO$_3$ 247.32 Calculated Value: C, 67.93; H, 6.94; N, 5.66; Observed Value: C, 67.92; H, 6.90; N, 5.73.

From the results of the ¹H-NMR spectrometry and the elementary analysis, the synthesis of the above described desired compound was confirmed.

Example 2

Synthetic Scheme of 2-Carboxyisopropyl Acrylamide

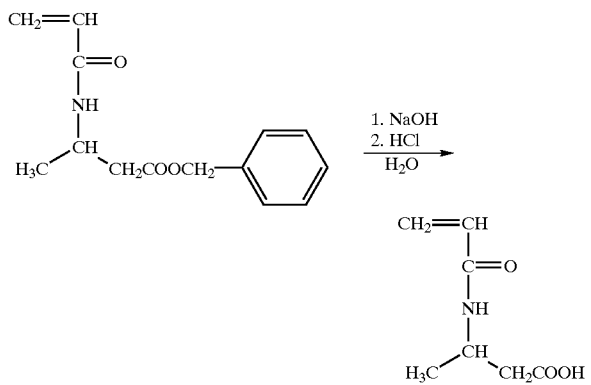

According to the above synthetic scheme, 1.0 g of the 2-(benzyloxycarbonyl)isoproypyl acrylamide as synthesized in Example 1 was dispersed in 50 ml of a 1N sodium hydroxide aqueous solution and stirred for one hour. After removal of the protective group of benzyl alcohol eliminated with the use of ether, concentrated hydrochloric acid was added such that the pH of the entire solution came to 2. After hydrogen chloride and water were completely distilled off, methanol was added to the residue and stirred for two hours. Only the methanol layer was separated and concentrated to obtain the desired 2-carboxyisopropyl acrylamide as a transparent viscous liquid. The structure was confirmed by using ¹H-NMR.

¹H-NMR δ (DMSO-d₆, ppm) 1.35 (d, 3H, C$\underline{H}_3$CHCH₂), 2.38 (m, 2H, CH₃CHC$\underline{H}_2$), 4.15 (m, 1H, CH₃C$\underline{H}$CH₂), 5.55, 6.06 and 6.12 (m, 3H, C$\underline{H}$=C$\underline{H}_2$), 8.10 (d, 1H, CON$\underline{H}$)

From the results of the ¹H-NMR spectrometry, the synthesis of the above described desired compound was confirmed.

Examples 3 and 4

In 35 ml of tetrahydrofuran were dissolved N-isopropyl acrylamide (abbreviated as "IPAAm") and 2-carboxyisopropyl acrylamide (abbreviated as "CIPAAm") in respective amounts as described in Table 3 and 11.5 mg of azobisisobutyronitrile (abbreviated as "AIBN") as the polymerization initiator, deaerated, sealed and then stirred at 65° C. for 2.5 hours. After the reaction, the precipitation of the reaction product into diethyl ether was twice repeated to effect purification.

TABLE 3

Synthesis of IPAAm/CIPAAm Copolymers

| Example | Amount of IPAAm (g) | Amount of CIPAAm (g) | Molar Ratio of IPAAm to CIPAAm in Obtained Copolymer | Yield (g) |
|---|---|---|---|---|
| 3 | 4.300 | 0.314 | 95.5:4.5 | 1.253 |
| 4 | 4.074 | 0.628 | 91.5:8.5 | 0.988 |

Examples 5 to 7

TABLE 4

Preparation of IPAAm/CIPAAm Copolymerization Crosslinked Products

| Example | Molar Ratio of IPAAm to CIPAAc | Amount of IPAAm (g) | Amount of CIPAAm (g) |
|---|---|---|---|
| 5 | 95:5 | 0.145 | 0.010 |
| 6 | 90:10 | 0.135 | 0.021 |
| 7 | 80:20 | 0.116 | 0.040 |

In a test tube N-isopropyl acrylamide (abbreviated as "IPAAm") and 2-carboxyisopropyl acrylamide in respective amounts as described in Table 4, 100 μl of a 26.6 mg/ml crosslinking agent, methylene-bisacrylamide (abbreviated as "MBAAm") aqueous solution and 4.8 μl of N,N,N',N'-tetramethylethylenediamine as the polymerization promoter were dissolved in 0.9 ml of water. After the resulting solution was bubbled with a nitrogen gas, 20 μl of a 40 mg/ml ammonium persulfate aqueous solution were immediately added thereto and then, the solution was drawn up in a capillary tube. The capillary tube was maintained at 0° C. for 24 hours and subsequently, a crosslinked product thus prepared was taken out of the capillary and dipped in cold water for one day to effect purification.

Example 8

Synthetic Scheme of 2-(Benzyloxycarbonyl) aminoisopropyl Acrylamide

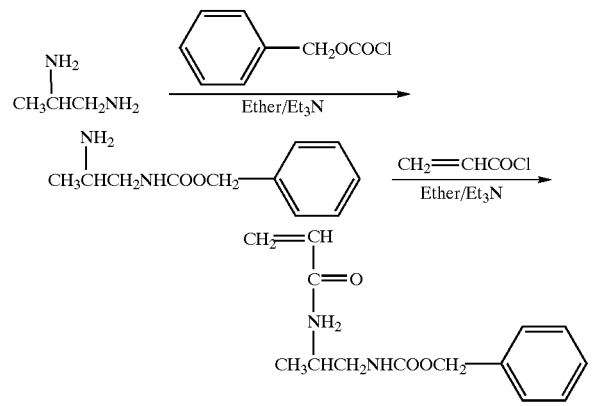

According to the above synthetic scheme, first, 119.4 ml of 1,2-diaminopropane purified by distillation and 194.9 ml of triethylamine were dissolved in 500 ml of dehydrated diethyl ether. To the resulting solution, 20 ml of carbobenzoxy chloride were slowly added dropwise at 0° C. and stirred at room temperature for 18 hours. The supernatant liquid was recovered, washed with water and then condensed. The addition of ethyl acetate separated out crystals which were then removed by filtration. The filtrate was condensed and purified by column chromatography to obtain 9.51 g of 1-(benzyloxycarbonyl)-amino-2-aminopropane as a transparent, colorless, viscous liquid. The synthesis is confirmed by the results of the $^1$H-NMR spectrometry set forth below.

$^1$H-NMR δ (DMSO-$d_6$, ppm) 0.91 (d, 3H, C$\underline{H}_3$CHCH$_2$), 2.80 (m, 1H, CH$_3$C$\underline{H}$CH$_2$), 2.85 (m, 2H, CH$_3$CHC$\underline{H}_2$), 5.01 (s, 2H, COOC$\underline{H}_2$-Φ), 7.35 (m, 5H, hydrogens on the benzene ring)

In 200 ml of diethyl ether were dissolved 8.0 g of 1-(benzyloxycarbonyl)amino-2-amonpropane and 8.0 ml of triethylamine, and 3.74 ml of acryloyl chloride were slowly added thereto dropwise. The resulting solution was stirred for two hours and condensed and ethyl acetate was added to the residue to dissolve. Furthermore, this solution was washed with water and dried with anhydrous sodium sulfate. The resulting product was purified by column chromatography to obtain 3.43 g of 2-(benzyloxycarbonyl)aminopropyl acrylamide as a plate crystal. The synthesis was confirmed by the results of the $^1$H-NMR spectrometry set forth below.

$^1$H-NMR δ (DMSO-$d_6$, ppm) 1.03 (d, 3H, C$\underline{H}_3$CHCH$_2$), 3.04 (m, 2H, CH$_3$CHC$\underline{H}_2$), 3.92 (m, 1H, CH$_3$C$\underline{H}$CH$_2$), 5.01 (m, 2H, COOC$\underline{H}_2$-Φ), 5.57, 6.07 and 6.18 (m, 3H, C$\underline{H}$=C$\underline{H}_2$), 7.34 (m, 5H, hydrogens on the benzene ring)

Example 9

Synthetic Scheme of 2-Aminoisopropyl Acrylamide

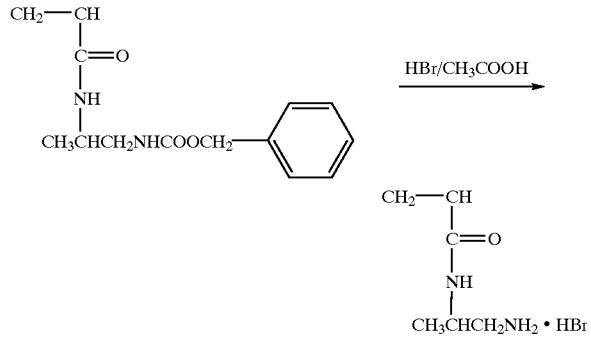

In a hydrogen bromide acetic acid solution was dispersed 1 g of the 2-(benzyloxycarbonyl)aminoisopropyl acrylamide synthesized in Example 8 and stirred for two hours. After hydrogen bromide and acetic acid were thoroughly distilled off, water was added to the residue. The protective group benzyl bromide eliminated with the use of ether was removed by extraction and subsequently, the aqueous layer was concentrated. Methanol was added to the residue and stirred for two hours. Only the methanol layer was separated and condensed to obtain the desired 2-aminoisopropyl acrylamide hydrobromate as a white solid. The structure was confirmed by using $^1$H-NMR.

$^1$H-NMR δ (DMSO-$d_6$, ppm) 1.35 (d, 3H, C$\underline{H}_3$CHCH$_2$), 2.89 (m, 2H, CH$_3$CHC$\underline{H}_2$), 4.21 (m, 1H, CH$_3$C$\underline{H}$CH$_2$), 5.50, 6.06 and 6.12 (m, 3H, C$\underline{H}$=C$\underline{H}_2$), 8.08 (d, 1H, CON$\underline{H}$)

From the results of the $^1$H-NMR spectrometry, the synthesis of the above described desired compound was confirmed.

Comparative Example 1 to 12

The N-isopropylacrylamide (abbreviated as "IPAAm")/acrylic acid (abbreviated as "AAc") copolymers and the N-isopropyl acrylamide as prepared in Reference Examples 1 to 4 were dissolved in a phosphoric acid buffer solution having a varied pH such that the concentration came to 0.6% by weight. The middle temperature between the temperature showing a transmittance of 90% and that showing a transmittance of 100% in the case of raising the temperature of the solution from 20° C. was regarded as a lower critical solution temperature (LCST). Furthermore, this range of temperature was regarded as an index of sensitivity to phase transition. In other words, smaller indices show that the phase transition has occurred in narrower ranges of temperature. The results of the measurement are set forth in Table 5.

TABLE 5

Evaluation of LCST and Sensitivity to Phase Transition of IPAAm/AAc Copolymers

| Comparative Example | Sample Used | pH of Solution | LCST (° C.) | Index of Sensitivity (° C.) |
|---|---|---|---|---|
| 1 | Reference Example 1 | 6.4 | 23.3 | 1.3 |
| 2 | Reference Example 2 | 6.4 | 28.1 | 1.8 |
| 3 | Reference Example 3 | 6.4 | 32.1 | 2.8 |
| 4 | Reference Example 4 | 6.4 | no phase transition occurred | |
| 5 | Reference Example 1 | 7.4 | 28.0 | 0.7 |
| 6 | Reference Example 2 | 7.4 | 32.9 | 2.4 |
| 7 | Reference Example 3 | 7.4 | 38.1 | 2.3 |
| 8 | Reference Example 4 | 7.4 | no phase transition occurred | |
| 9 | Reference Example 1 | 9.0 | 30.0 | 0.8 |
| 10 | Reference Example 2 | 9.0 | 35.8 | 2.8 |
| 11 | Reference Example 3 | 9.0 | no phase transition occurred | — |
| 12 | Reference Example 4 | 9.0 | no phase transition occurred | |

Examples 10 to 15

TABLE 6

Evaluation of LCST and Sensitivity to Phase Transition of IPAAm/CIPAAm Copolymers

| | Sample Used | pH of Solution | LCST (° C.) | Index of Sensitivity (° C.) |
|---|---|---|---|---|
| Example 10 | Example 3 | 6.4 | 23.4 | 0.7 |
| Example 11 | Example 4 | 6.4 | 23.3 | 0.8 |
| Comparative Example 1 | Reference Example 1 | 6.4 | 23.3 | 1.3 |
| Example 12 | Example 3 | 7.4 | 27.7 | 0.2 |
| Example 13 | Example 4 | 7.4 | 27.3 | 0.9 |
| Comparative Example 5 | Reference Example 1 | 7.4 | 28.0 | 0.7 |
| Example 14 | Example 3 | 9.0 | 29.7 | 0.4 |
| Example 15 | Example 4 | 9.0 | 30.3 | 0.3 |
| Comparative | Reference | 9.0 | 30.0 | 0.8 |

TABLE 6-continued

Evaluation of LCST and Sensitivity to Phase Transition of IPAAm/CIPAAm Copolymers

| Sample Used | pH of Solution | LCST (° C.) | Index of Sensitivity (° C.) |
|---|---|---|---|
| Example 9 | Example 1 | | |

The N-isopropyl acrylamide (abbreviated as "IPAAm")/2-carboxyisopropyl acrylamide (abbreviated as "CIPAAm") copolymers as prepared in Examples 3 and 4 were dissolved in a phosphoric acid buffer solution having a varied pH such that the concentration came to 0.6% by weight. The LCST and the index of sensitivity to phase transition were evaluated in the same manner as in Comparative Examples 1 to 12. The results of the measurement are set forth in Table 6. In order to compare the IPAAm/CIPAAm copolymers with the IPAAm homopolymer, the results of Comparative Examples 1, 5 and 9 as well are set forth in the Table.

As would be clear from Table 6 and Table 5 of Comparative Examples, the copolymers composed of N-isopropyl acrylamide (IPAAm) and 2-carboxyisopropyl acrylamide (CIPAAm) having a similar structure thereto as obtained in the Examples even at a content of CIPAAm of about 10 mol % cause phase transition at a temperature approximately equal to the temperature at which the phase transition is observed with the IPAAm homopolymer and, in addition, at the time of causing the phase transition, the range of temperature is extremely narrow and accordingly, these copolymers are diametrically different from the copolymers of IPAAm and acrylic acid in Comparative Example.

Comparative Examples 13 to 16

In a pH 6 phosphoric acid buffer solution, the degree of equilibrium swell of the N-isopropyl acrylamide (IPAAm)/acrylic acid (AAc) copolymerization crosslinked products of Reference Examples 5 to 8 at each temperature ranging from 10° C. to 50° C. was measured. The term "degree of equilibrium swell" as used herein is defined as the value $[(d/d_0)^3]$ of the cube of the value obtained by dividing the diameter (d) attaining an equilibrium at each temperature by the initial diameter ($d_0$) corresponding to the diameter of the capillary tube in the preparation of the crosslinked products in Reference Examples 5 to 8. The results are set forth in FIG. 1.

Comparative Examples 17 to 20

In a pH 7.4 phosphoric acid buffer solution, the degree of equilibrium swell of the N-isopropyl acrylamide (IPAAm)/acrylic acid (AAc) copolymerization crosslinked products of Reference Examples 5 to 8 at each temperature ranging from 10° C. to 50° C. was measured. The term "degree of equilibrium swell" as used herein has the same definition as in Comparative Examples 13 to 16. The results are set forth in FIG. 2.

Comparative Examples 21 to 24

In a pH 9.0 phosphoric acid buffer solution, the degree of equilibrium swell of the N-isopropyl acrylamide (IPAAm)/acrylic acid (AAc) copolylmerization crosslinked products of Reference Examples 5 to 8 at each temperature ranging from 10° C. to 50° C. was measured. The term "degree of equilibrium swell" as used herein has the same definition as in Comparative Examples 13 to 16. The results are set forth in FIG. 3.

Examples 16 to 18

In a pH 6.4 phosphoric acid buffer solution, the degree of equilibrium swell of the N-isopropyl acrylamide (IPAAm/2-carboxyisopropyl acrylamide (CIPAAm) copolylmerization crosslinked products of Examples 5 to 7 at each temperature ranging from 10° C. to 50° C. was measured. The term "degree of equilibrium swell" as used herein has the same definition as in Comparative Examples 13 to 16. The results are set forth in FIG. 1.

Examples 19 to 21

In a pH 7.4 phosphoric acid buffer solution, the degree of equilibrium swell of the N-isopropyl acrylamide (IPAAm/2-carboxy-isopropyl acrylamide (CIPAAm) copolylmerization crosslinked products of Examples 5 to 7 at each temperature ranging from 10° C. to 50° C. was measured. The term "degree of equilibrium swell" as used herein has the same definition as in Comparative Examples 13 to 16. The results are set forth in FIG. 2.

Examples 22 to 24

In a pH 9.0 phosphoric acid buffer solution, the degree of equilibrium swell of the N-isopropyl acrylamide (IPAAm/2-carboxyisopropyl acrylamide (CIPAAm) copolylmerization crosslinked products of Examples 5 to 7 at each temperature ranging from 10° C. to 50° C. was measured. The term "degree of equilibrium swell" as used herein has the same definition as in Comparative Examples 13 to 16. The results are set forth in FIG. 3.

Figure 2:
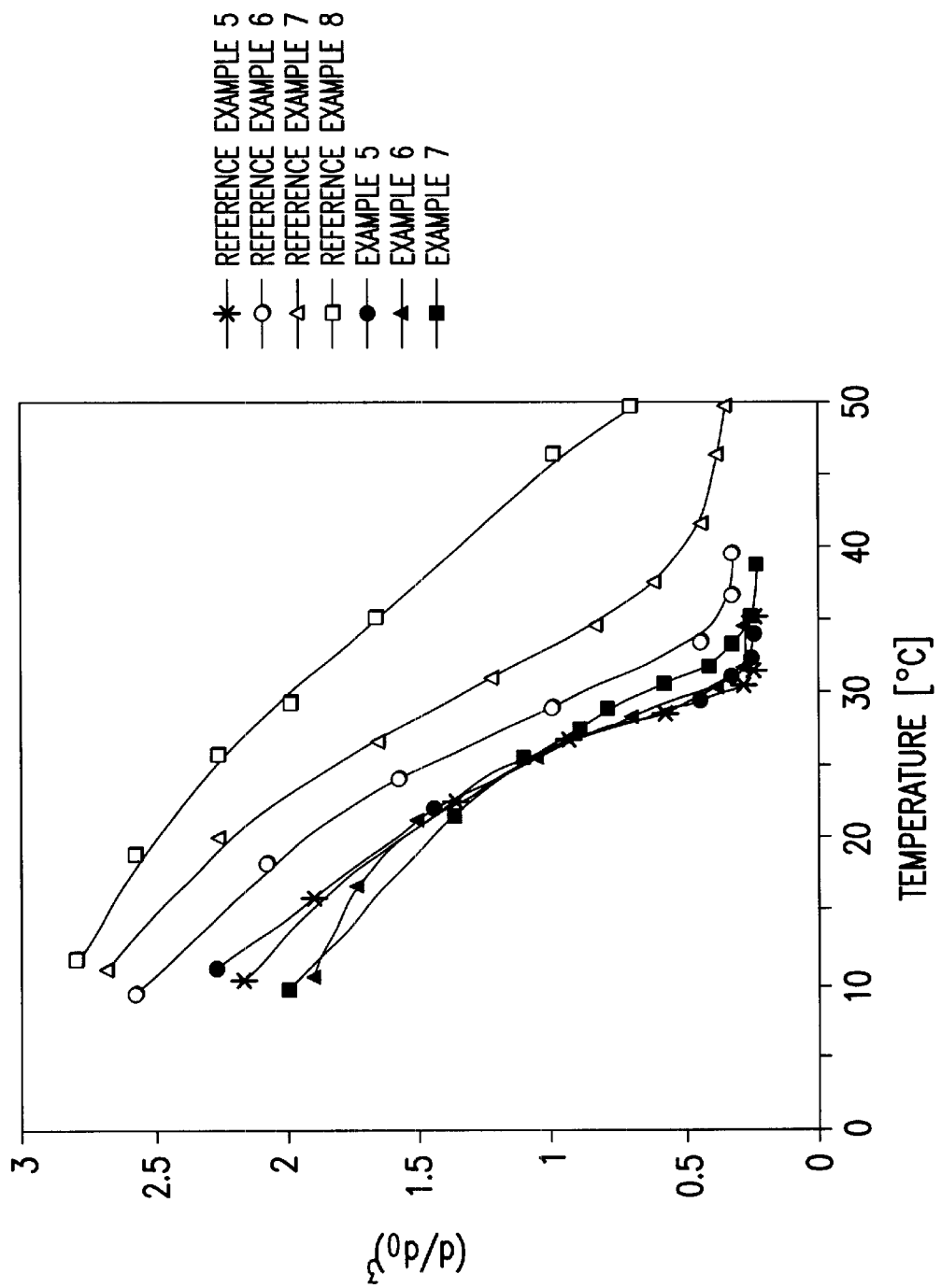
FIG. 2 is a graph showing the equilibrium swell of each crosslinked product in a phosphate buffer at pH 7.4.
Figure 3:
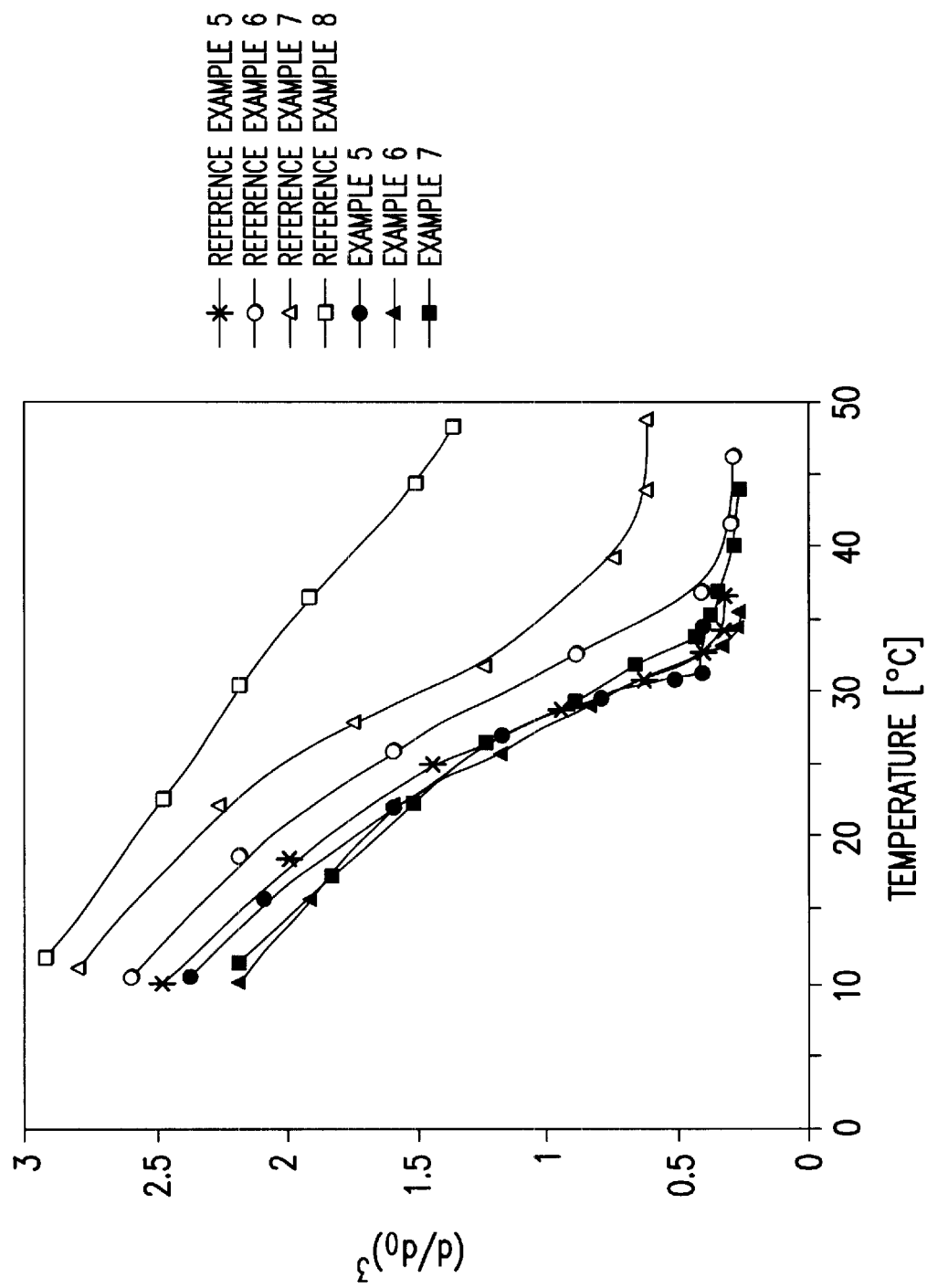
FIG. 3 is a graph showing the equilibrium swell of each crosslinked product in a phosphate buffer at pH 9.0.

FIGS. 1 to 3 have shown that in the copolymerization crosslinked products comprising N-isopropyl acrylamide and acrylic acid, with increased contents of acrylic acid, the temperature to complete the change in volume moves toward higher temperatures and the change in degree of equilibrium swell at each temperature also tends to no longer be sharp. In contrast to this, in the copolymerization crosslinked products comprising N-isopropyl acrylamide (IPAAm) and 2-carboxyisopropyl acrylamide (CIPAAm), the change in volume has been completed at the same temperature as in the IPAAm homopolymerization crosslinked product and the change in degree of equilibrium swell as well has been sharp. In other words, crosslinked products exhibiting the same behavior in the extremely sharp change in volume as the IPAAm homopolymerization crosslinked product could be obtained in spite of their having a carboxyl group rich in reactivity.

Industrial Applicability

The present invention made it possible to provide monomers for preparing polymers or hydrogels (i.e. crosslinked products) incorporating many functional groups while maintaining the sensitive temperature response, and said polymers or hydrogels (i.e. crosslinked products).

What is claimed is:
1. An acrylamide derivative of the following general formula (I):

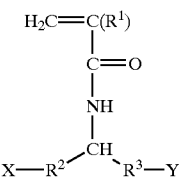

(I)

wherein $R^1$ represents a hydrogen atom, a straight-chain or branched alkyl group containing 1 to 6 carbon atoms or a C3–6 cycloalkyl group, $R^2$ and $R^3$ each independently represent an alkylene group containing 1 to 6 carbon atoms or $R^2$ and $R^3$ may be combined to form a ring, X represents a hydrogen atom, an amino group, a hydroxyl group, a carboxyl group or a —COOR$^4$ group wherein $R^4$ represents a C1–6 straight-chain or branched alkyl. C3–6 cycloalkyl, phenyl, substituted phenyl, benzyl or substituted benzyl group, and Y represents an amino group, a hydroxyl group, a carboxyl group or a —COOR$^4$ group wherein $R^4$ represents a C1–6 straight-chain or branched alkyl, C3–6 cycloalkyl, phenyl, substituted phenyl, benzyl or substituted benzyl group, with the proviso that when X or Y is a hydroxyl group, $R^2$ or $R^3$ is not a methylene group or $R^2$ and $R^3$ are not combined to form a cyclohexyl ring.

2. A polymer consisting of repeating identical or different units of the following general formula (II):

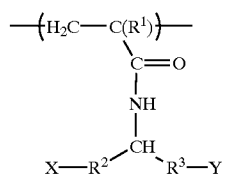

(II)

wherein $R^1$ represents a hydrogen atom, a straight-chain or branched alkyl group containing 1 to 6 carbon atoms or a C3–6 cycloalkyl group, $R^2$ and $R^3$ each independently represent an alkylene group containing 1 to 6 carbon atoms or $R^2$ and $R^3$ may be combined to form a ring, X represents a hydrogen atom, an amino group, a hydroxyl group, a halogen atom, a carboxyl group or a —COOR$^4$ group wherein $R^5$ represents a C1–6 straight-chain or branched alkyl, C3–6 cycloalkyl, phenyl, substituted phenyl, benzyl or substituted benzyl group, and Y represents an amino group, a hydroxyl group, a halogen atom, a carboxyl group or a —COOR$^4$ group wherein $R^4$ represents a C1–6 straight-chain or branched alkyl, C3–6 cycloalkyl, phenyl, substituted phenyl, benzyl or substituted benzyl group, with the proviso that when X or Y is a hydroxyl group, $R^2$ or $R^3$ is not a methylene group.

3. A copolymer consisting of identical or different repeating units of the formula (II) in claim 2 and identical or different repeating units of general formula (III):

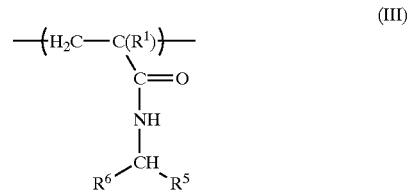

(III)

wherein $R^1$ represents a hydrogen atom, or a straight-chain or branched alkyl group containing 1 to 6 carbon atoms or a C3–6 cycloalkyl group, $R^5$ represents a straight-chain or branched alkyl group containing 1 to 6 carbon atoms or a C3–6 cycloalkyl group, and $R^6$ represents a straight-chain or branched alkyl group containing 1 to 6 carbon, atoms or a C3–6 cycloalkyl group, or $R^5$ and $R^6$ may be combined to form a 3-, 4-, 5- or 6-membered ring in which the —CH— group to which they are attached is one member.

4. The copolymer of claim 3 wherein the repeating unit of general formula (III) is N-isopropyl acrylamide.

5. A crosslinked product containing the polymer of claim 2.

6. A crosslinked product containing the copolymer of claim 3.

7. The crosslinked product of claim 6 wherein the repeating unit of general formula (III) is N-isopropyl acrylamide.

8. The acrylamide derivative of claim 1 wherein X or Y is a carboxyl group.

9. The polymer of claim 2 wherein X or Y is a carboxyl group.

10. The copolymer of claim 3 wherein X or Y is a carboxyl group.

* * * * *

UNITED STATES PATENT AND TRADEMARK OFFICE
CERTIFICATE OF CORRECTION

PATENT NO.    : 6,495,645 B1
DATED         : December 17, 2002
INVENTOR(S)   : Okano et al.

It is certified that error appears in the above-identified patent and that said Letters Patent is hereby corrected as shown below:

<u>Title page,</u>
Please change "[73] Assignee: Terou Okano, Ichikawa (JP)" to read
-- [73] Assignee: Teruo Okano, Ichikawa (JP) --

Signed and Sealed this

Twenty-seventh Day of May, 2003

JAMES E. ROGAN
*Director of the United States Patent and Trademark Office*